US009389171B2

(12) United States Patent
Degner et al.

(10) Patent No.: US 9,389,171 B2
(45) Date of Patent: Jul. 12, 2016

(54) DEVICE FOR HIGH-RESOLUTION DETERMINATION OF THE CONCENTRATION OF SUBSTANCES IN FLUID MEDIA

(71) Applicant: Bluepoint-Medical GmbH & Co. KG, Selmsdorf (DE)

(72) Inventors: Martin Degner, Kroepelin (DE); Nils Damaschke, Papendorf (DE); Hartmut Ewald, Rostock (DE)

(73) Assignee: Bluepoint-Medical GmbH & Co. KG, Selmsdorf (DE)

( * ) Notice: Subject to any disclaimer, the term of this patent is extended or adjusted under 35 U.S.C. 154(b) by 0 days.

(21) Appl. No.: 13/655,305

(22) Filed: Oct. 18, 2012

(65) Prior Publication Data

US 2013/0100452 A1  Apr. 25, 2013

(30) Foreign Application Priority Data

Oct. 19, 2011 (DE) .......................... 10 2011 116 367

(51) Int. Cl.
*G01N 21/59* (2006.01)
*G01N 21/27* (2006.01)
*G01J 3/42* (2006.01)
*G01N 21/31* (2006.01)
*G01N 21/33* (2006.01)
*G01N 21/3577* (2014.01)
*G01J 3/10* (2006.01)

(52) U.S. Cl.
CPC ................ *G01N 21/274* (2013.01); *G01J 3/42* (2013.01); *G01N 21/314* (2013.01); *G01N 21/33* (2013.01); *G01N 21/3577* (2013.01); *G01J 3/10* (2013.01); *G01N 2201/062* (2013.01); *G01N 2201/0624* (2013.01)

(58) Field of Classification Search
CPC .......... G01N 2201/0625; G01N 21/27; G01N 21/3577; G01N 21/59; G01N 21/85; G01N 21/53
USPC .................................................. 356/432–440
See application file for complete search history.

(56) References Cited

U.S. PATENT DOCUMENTS

| 4,195,932 | A | * | 4/1980 | Popelka .......................... 356/407 |
| 4,867,559 | A | * | 9/1989 | Bach ................................ 356/73 |
| 5,381,010 | A | * | 1/1995 | Gordon .......................... 250/343 |
| 6,791,689 | B1 | * | 9/2004 | Weckstrom ..................... 356/437 |
| 2003/0205673 | A1 | * | 11/2003 | Williams ........................ 250/343 |
| 2005/0190372 | A1 | * | 9/2005 | Dogariu .......................... 356/479 |
| 2006/0103850 | A1 | * | 5/2006 | Alphonse et al. .............. 356/479 |
| 2008/0198360 | A1 | * | 8/2008 | Dosmann et al. ................ 356/39 |
| 2011/0149289 | A1 | * | 6/2011 | Carson et al. .................. 356/437 |
| 2012/0006098 | A1 |   | 1/2012 | Degner et al. |

FOREIGN PATENT DOCUMENTS

EP        1 729 110 A2   12/2006
WO    WO 2006/037985     4/2006

OTHER PUBLICATIONS

Lester S. D., et al., "High-Efficiency Ingan MQW Blue and Green LEDs", Journal of Crystal Growth, vol. 189-190, No. 15, pp. 786-789 (Jun. 1998).
Nakamura S., et al., "High-Brightness Ingan Blue, Green, and Yellow Light-Emitting Diodes with Quantum Well Instructures", Japanese Journal of Applied Physics, vol. 34, No. 7A, Part 2, pp. L797-L799 (Jul. 1995).
Yamada M., et al., "Phosphor Free High-Luminous-Efficiency White Light-Emitting Dioades Composed of Ingan Mutli-Quantum Well", Japanese Journal of Applied Physics, vol. 41, No. 3A, Part 2, pp. L246-L249 (Mar. 2002).

* cited by examiner

*Primary Examiner* — Hoa Pham
(74) *Attorney, Agent, or Firm* — Chalin A. Smith; Smith Patent (57) ABSTRACT

The present invention relates to a device for determining the concentration of substances in fluid media.

15 Claims, 8 Drawing Sheets

DEVICE FOR HIGH-RESOLUTION DETERMINATION OF THE CONCENTRATION OF SUBSTANCES IN FLUID MEDIA

PRIORITY

This application claims the priority, under 35 U.S.C. §119, of German patent application No. 10 2011 116 367.4 filed Oct. 19, 2011; the entire disclosure of the prior application is herewith incorporated by reference.

FIELD OF THE PRESENT INVENTION

The present invention relates to a device for determining the concentration of substances in fluid media.

BACKGROUND OF THE PRESENT INVENTION

The underlying method of optical absorption spectroscopy is generally known and is also used in various arrangements for determining the concentration of substances. The light sources used for these systems include broadband light sources, such as thermal emitters and various kinds of gas-discharge lamps (EP 0 656 535 A1), and narrow-band laser light sources (Lambrecht, A. and J. Koeth, *Quantum cascade laser—a new laser light source for optical analytical measuring*. Technisches Messen, 2005). Recently, LEDs have also been used as spectrally selective light sources for substances with mainly comparatively broadband absorption characteristics (DE 10 2008 064 173 A1). However, many substances have comparatively narrow-band absorption characteristics relative to the spectral bandwidth of the LED light source, such as for example dissolved benzene (generally designated hereinafter as "narrow-band", and the opposite case as "broadband").

In absorptiometry, high measurement accuracy for determining the concentration of substances in fluid media requires high raw signal resolution and raw signal stability, which is not directly achievable based on the emission stability of conventional light sources used in spectroscopy. Emission stability means an emission spectrum that is stable with respect to the selected measurement wavelengths for the measurement time, and amplitudes of these wavelengths that are stable for the measurement time.

Determination of the concentration of substances is based on measurement of the attenuation of light, caused by the light absorption of the substance at a specified concentration. Conventionally, steps are taken for referencing the emission properties of the light source, so as to compensate source-induced disturbing effects with respect to emission stability in the measurement signal. In conventional arrangements, for this purpose the light is for example divided between source and optical measuring path and partly directed onto a reference detector. Therefore in addition to the increased technical expense for the optical beam guidance, two receiving units working exactly identically are also required. The resultant measuring systems are therefore often very complex and of intricate mechanical construction and therefore also of high cost. This applies in particular for example to systems based on broadband light sources and the receiving units often used here, based on a spectrometer.

Another solution in conventional systems is based on mechanical switches in the optical beam path. In this way it is possible to perform referencing of the light used for measurement with just one detector unit. In this case, however, there are high requirements on the reproducibility of the switching operation, to ensure spectral and amplitude stability. Continuous determination of the concentration of substances with high resolution is not possible here, owing to the time taken for referencing.

Changes in the transmission of the absorption measuring path or of the reference measuring path and changes, for example ageing, of the detector unit(s) have a direct influence on measurement accuracy. This necessitates regular, cyclic recalibration of the whole system.

Another basic possibility for achieving high measurement accuracy in absorption measurements consists of utilising the wavelength-specific absorption of the substance, so as to compensate amplitude fluctuations of the source, of the optical path and of the detectors. However, this requires high spectral resolution of the measuring system and therefore a high level of instrumentation and the associated high costs, for example the use of very-high-resolution spectrometers, with a spectral resolution of typically 0.01 nm or less.

The use of narrow-band laser light sources for laser absorption spectroscopy is, along with the arrangements described already based on broadband light sources, another method often used for determining the concentration of substances in fluid media. An exemplary embodiment of this is TDLAS (tunable laser absorption spectroscopy). In systems corresponding to this method, the emission wavelength of a suitable laser light source is modulated spectrally for example by means of the current the temperature [sic]. In this way, an absorption peak of the substance to be measured is sampled at different wavelengths. By comparing with known spectra, disturbances can largely be suppressed and the concentration of substances can be determined.

High-resolution concentration measurements are performed using this method. An important drawback of this measurement technique is the availability of economical laser light sources for certain wavelengths. Therefore this method is only available for selected substances and is, for example when using quantum-cascade lasers, extremely expensive. This method of measurement is, in addition, restricted in the measuring rate owing to the time-dependent wavelength modulation of the source, and there is no continuous determination of concentration.

To summarise, from the prior art, for high-resolution determination of the concentration of substances with primarily narrow-band absorption characteristics (for example benzene, toluene), there are the following disadvantages: conventional broadband light sources must be referenced both with respect to the total emission intensity and with respect to the spectral distribution of the emission intensity. Possibilities for referencing that may be considered require a certain proportion of light and/or measuring time and therefore reduce the signal/noise ratio of the measurement signal and/or the temporal resolution of the measurement signal (measuring rate). Each referencing is basically associated with a not inconsiderable expenditure of effort and associated costs and for example increases the complexity of the whole system and correspondingly also the vulnerability of the system.

Generally, devices based on broadband light sources or lasers, compared to LED-based systems, are as a rule much more expensive, less mechanically robust, more prone to interference and are comparatively large and have higher power consumption. The electronic controls for LED-based measuring systems are also much less expensive.

Figure 1:
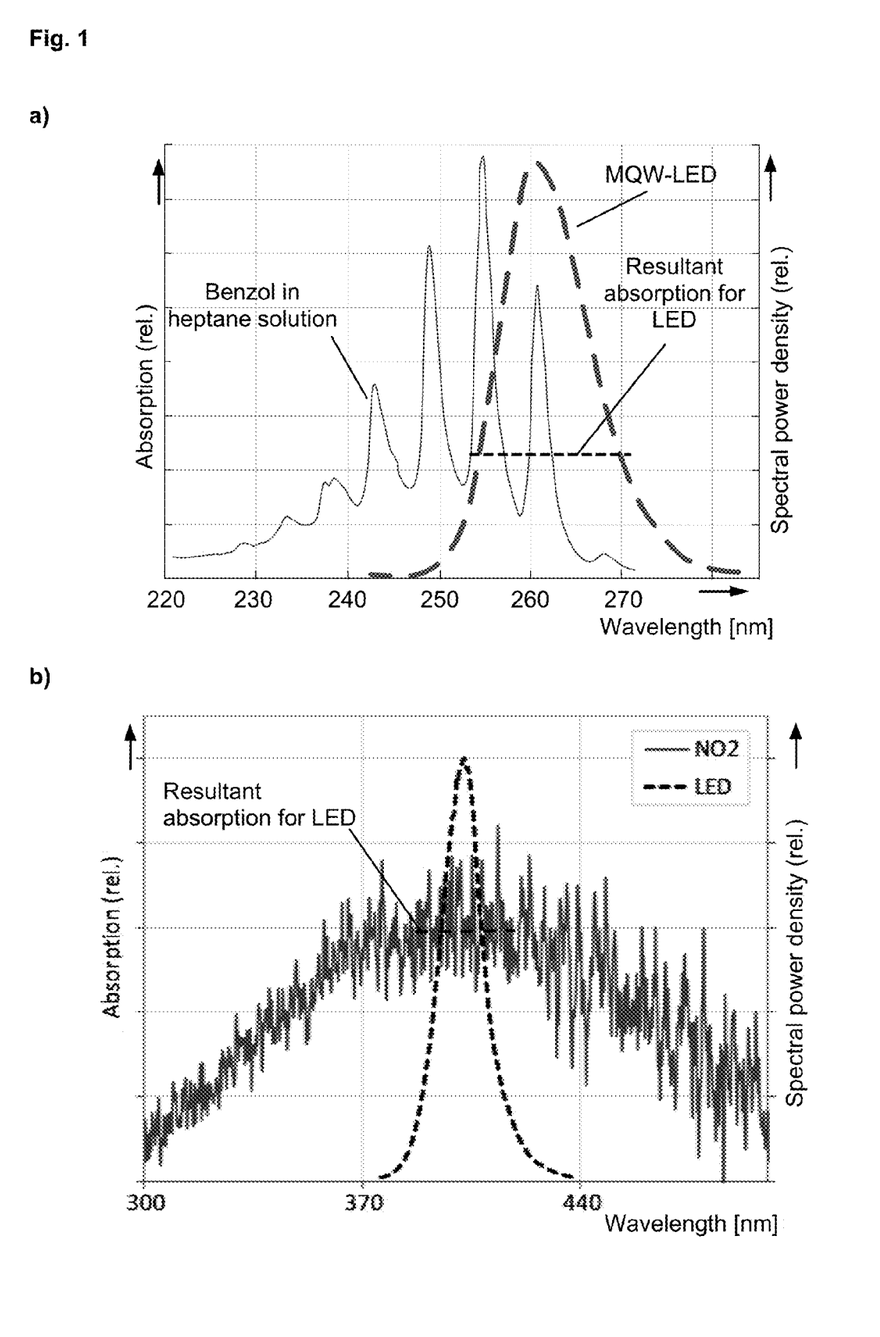
FIG. 1 shows a comparison of the resultant absorption cross-section for benzene or $NO_2$ for an LED-absorption arrangement.

The known LED-based absorption spectroscopy (DE 10 2008 064 173 A1) is not, however, very suitable for high measurement accuracy in particular for substances with very narrow-band absorption characteristics owing to the resultant small absorption cross-section. The resultant absorption cross-section of a measuring system, consisting of the emission characteristics of the LED and the absorption property of the substance to be determined, is found from the attenuation of the transmission signal in the system. In this connection, FIG. 1 shows a comparison of the resultant absorption cross-section for benzene or $NO_2$ for an LED-absorption arrangement. As noted below, FIG. 1a shows the example of narrow-band absorption characteristics of benzene. The resultant absorption is much less than the peak absorption. FIG. 1b shows the example of broadband absorption characteristics of $NO_2$. The resultant absorption is similar to the peak absorption.

In addition, the necessary referencing requires a proportion of the light output that is not negligible. Especially in the case of measuring tasks in the mid-infrared or in the UV, the luminous efficiency of the LED sources is generally not very high and the light output available for the measurement has a decisive influence on the resultant measurement accuracy and resolution of the measurement signal.

SUMMARY OF THE PRESENT INVENTION

There is therefore still the problem of detecting, and determining quantitatively, various substances in fluid media free from interference, with high resolution of the measurement signal and in a robust set-up that is simple to implement. This problem is solved with the device according to the present invention, more particularly a device for determining the concentration of one or more substances in a fluid medium characterised in that the light emission of an MQW LED is used for absorption measurement, wherein the emitted light interacts in a measuring system with the substance to be determined, acts, in a detector unit by means of an optical filter, upon an absorption detector and a reference detector, which generate a measurement signal and a reference signal, and the concentration of the substance to be determined is found by comparing these signals.

BRIEF DESCRIPTION OF THE DRAWINGS

FIG. 1a shows the example of narrow-band absorption characteristics of benzene. The resultant absorption is much less than the peak absorption. FIG. 1b shows the example of broadband absorption characteristics of $NO_2$. The resultant absorption is similar to the peak absorption.

FIG. 2a shows the spectral power density distribution as a function of temperature for a standard LED. It can be seen that the emission spectrum is not spectrally stable. In contrast, the emission spectrum of an MQW LED, as shown in FIG. 2b, is spectrally stable over a wide temperature range.

FIG. 4a shows a transmission arrangement with a collimator section, and on the other hand, FIG. 4b shows a holomirror reflection arrangement. Whereas in the arrangement according to a), the absorption length can be adapted at will to the application, the arrangement according to b) has the advantages that here only one access to the measuring point is required and that no errors caused by dispersion can occur.

FIG. 8).

DETAILED DESCRIPTION OF PREFERRED EMBODIMENT

The device according to the invention is suitable primarily for substances with comparatively narrow-band absorption characteristics relative to the spectral bandwidth of the LED light source (for example dissolved benzene).

The use of multiple-quantum-well (MQW) LEDs as the light source for high-resolution, stable optical spectroscopy did not at first seem suitable, as MQW LEDs are not stable light sources with respect to their emission intensity. The light emission is for example strongly temperature-dependent.

Figure 2:
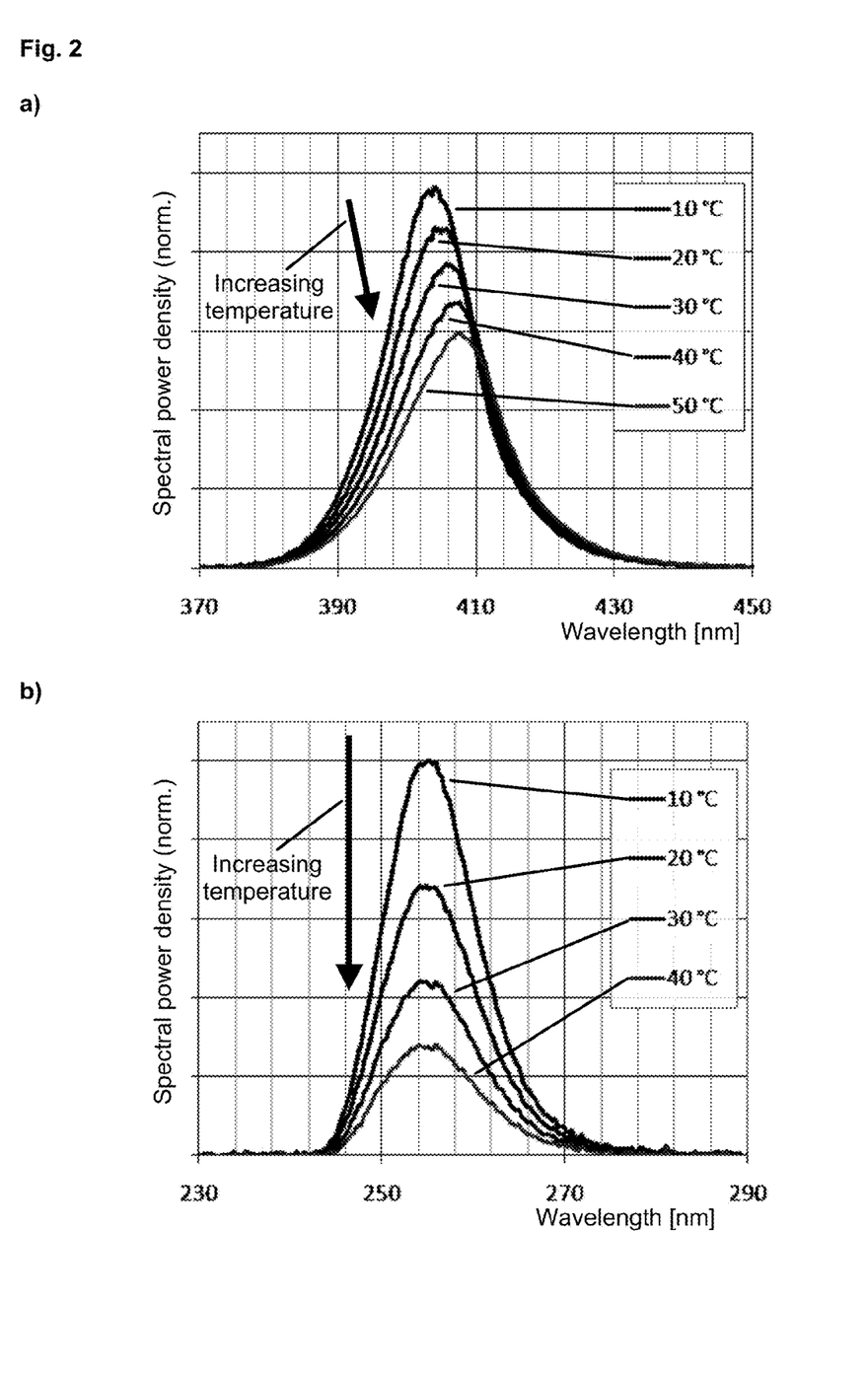

It has now been found that the high spectral emission stability of MQW LEDs can be utilised for overcoming this drawback. Spectral emission stability means an emission spectrum that is stable with respect to the selected measurement wavelengths for the measurement time and over a wide temperature range. This effect is explained in FIG. 2. As noted above, FIG. 2a shows the spectral power density distribution as a function of temperature for a standard LED. It can be seen that the emission spectrum is not spectrally stable. In contrast, the emission spectrum of an MQW LED, as shown in FIG. 2b, is spectrally stable over a wide temperature range.

Under normal operating conditions, amplitude fluctuations occur in the percentage range. High-resolution concentration measurements, however, typically require a stability of the source with respect to the amplitudes of the measurement wavelengths of less than 10 ppm.

The device of the present invention described herein, suitable for determining the concentration of one or more substances in a fluid medium, utilises the very high spectral stability of MQW LEDs in conjunction with at least one optical filter for amplitude referencing. For this, the LED emission spectrum is divided into at least two parts; one part is used for the absorption measurement of the substance to be determined, and the second part is used for referencing the amplitude fluctuations of the emission intensity. Disturbances of the transmission signal in the whole system are also largely eliminated as a result.

With this comparatively simple device and its inexpensive components, it is thus possible to perform high-resolution concentration measurements of substances, which otherwise are only possible with very sophisticated equipment.

Compared to conventional measuring systems for determining the concentration of substances in fluid media, the device according to the invention offers the following advantages, among others:

The referencing and compensation of amplitude fluctuations of the light source takes place almost without restriction of the light output (emission intensity) available for the absorption measurement, resulting in a favourable signal/noise ratio (SNR) or a high resolution of the measurement signal.

Changes of the measurement signal caused for example by ageing of the detector unit and/or of the optical components and contamination of the optical system are compensated.

MQW LEDs are very inexpensive and easy to control, for example compared to lasers.

MQW LEDs are available in a very extensive spectral range from the ultraviolet (UV) to the infrared wavelength region (IR). Therefore a corresponding arrangement, in contrast for example to TDLAS, can be designed for a large number of substances.

The spectrally limited emission bandwidth of the MQW LEDs means that only small requirements are imposed on the spectral blocking range of the optical filters, which can therefore be produced much more economically.

Owing to the spectrally limited emission bandwidth of the MQW LEDs, it is also possible to use edge filters instead of bandpass filters, in order to produce two delimited wavelength ranges (for the absorption measurement and the reference measurement).

Inexpensive standard photodetectors can be used as detectors.

The device makes continuous concentration measurement possible.

No mechanically moving components are required.

MQW LEDs can be modulated very well electronically, for example compared to thermal light sources. They can thus have low susceptibility to interference and an improved SNR.

It is possible to combine several MQW LEDs for simultaneous detection of various substances in one optical set-up.

Using MQW LEDs, it is possible to produce a small, mechanically robust set-up with low electrical power consumption. Corresponding arrangements can be used for example in battery-operated instruments.

Figure 3:
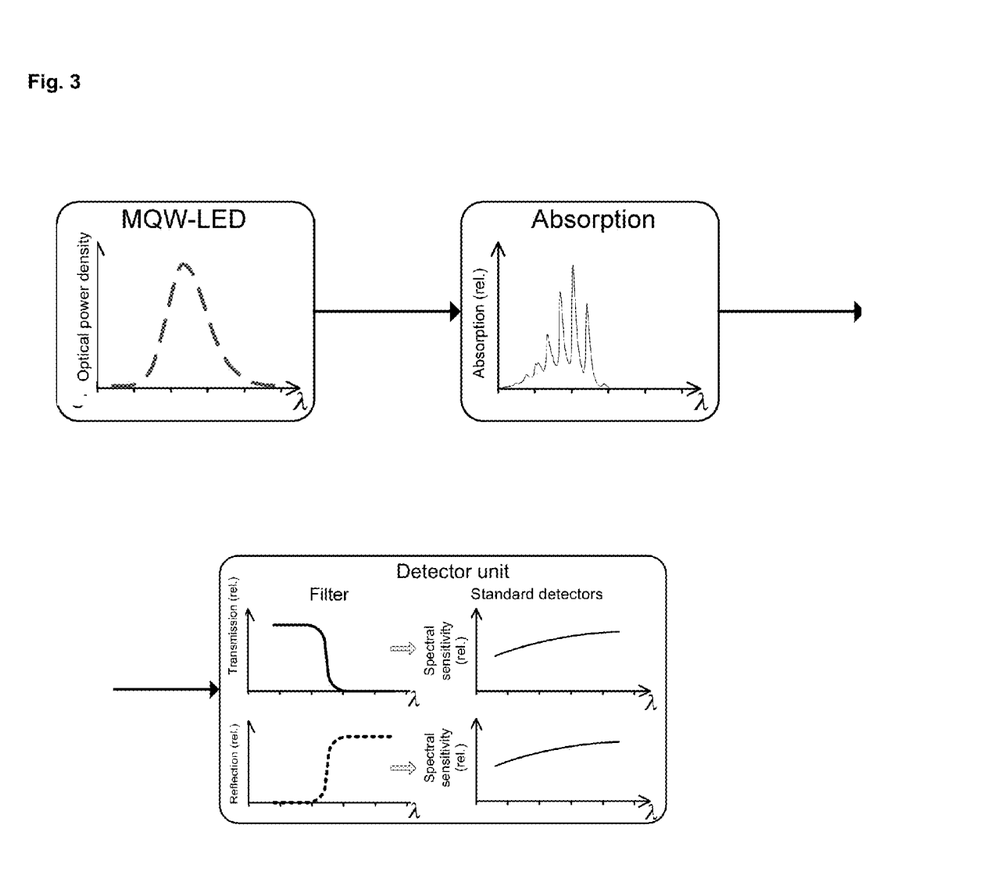
FIG. 3 shows a reduced block diagram of the device according to the invention. The spectral characteristics of the individual modules and the absorption of the medium to be detected are shown schematically.

As noted above, FIG. 3 shows a reduced block diagram of the device according to the invention. The spectral characteristics of the individual modules and the absorption of the medium to be detected are shown schematically. The light emitted by the MQW LED is accordingly led directly through a system for absorption measurement onto the detector unit. Spectrally broadband, non-selective standard photodetectors can be used for the measurement set-up.

In the detector unit, the light is divided spectrally by means of a reflection filter, as will be explained in more detail in FIGS. 5 and 6. The spectral reference is formed in the detector unit by means of the reflection filter. Both the light used for the absorption measurement and the light used for the reference measurement pass through the complete set-up to the detector unit on the same path. Possible dispersive interfering effects in the system have hardly any effects on the measurement signal, owing to the restricted emission spectrum of the MQW LEDs. Almost all fluctuations or disturbances in the MQW LED set-up have identical effects on the absorption path and the reference path and are compensated. Therefore they do not, or do not significantly, influence the measurement signal.

Figure 4:
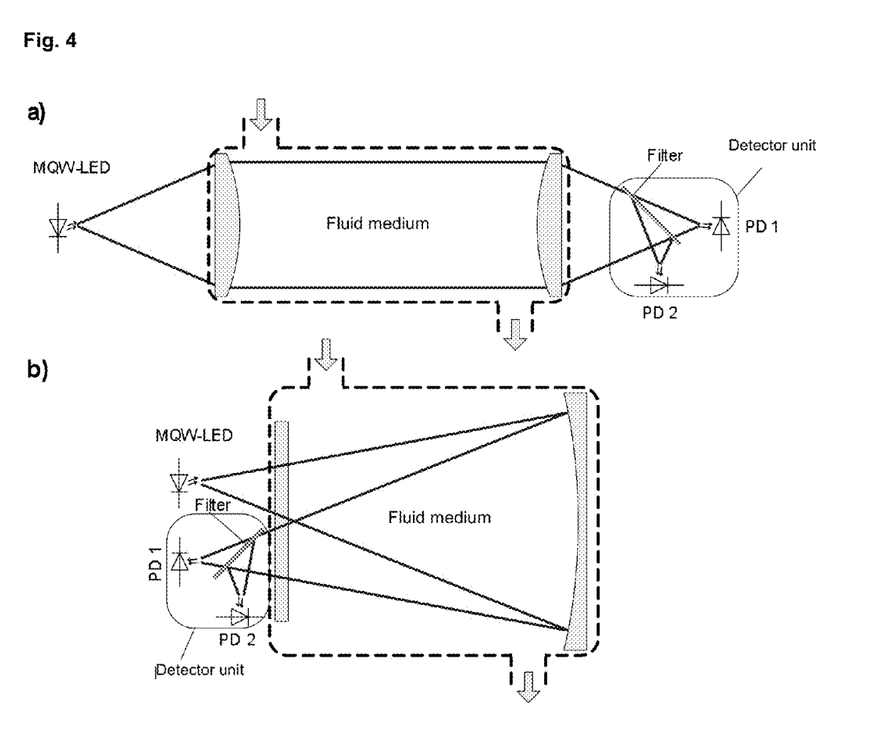
FIG. 4 shows two exemplary embodiments of the device according to the invention. On the one hand.

As noted above, FIG. 4 shows two exemplary embodiments of the device according to the invention. On the one hand, FIG. 4a shows a transmission arrangement with a collimator section, and on the other hand, FIG. 4b shows a holomirror reflection arrangement. Whereas in the arrangement according to a), the absorption length can be adapted at will to the application, the arrangement according to b) has the advantages that here only one access to the measuring point is required and that no errors caused by dispersion can occur.

The filter-detector system contained in both arrangements, consisting of the photodetector 1 (PD 1), the photodetector 2 (PD 2) and the filter, can for example be produced as a unit a few millimeters in size, in microsystems technology. In this way, the detector unit can be of very compact and mechanically robust construction and can easily be integrated in the optical system.

The optical filter used in the device according to the invention is preferably designed as a reflection filter, so that both the transmitted and the reflected light can be used. The filter can be designed as a bandpass filter or as an edge filter (short-wavelength pass or long-wavelength pass) with high edge steepness. Corresponding filters are for example already known from Raman spectroscopy.

Figure 5:
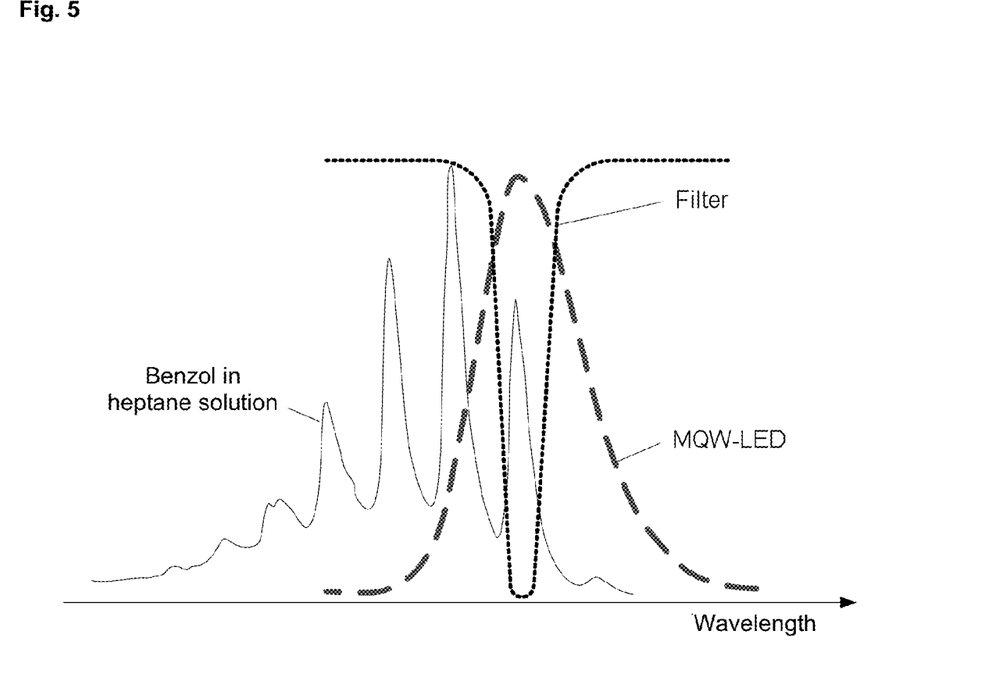
FIGS. 5 and 6 are a graphic representation of a detector unit in which the light is divided spectrally by means of a reflection filter, namely a bandpass filter (FIG. 5) or an edge filter (FIG. 6).
Figure 6:
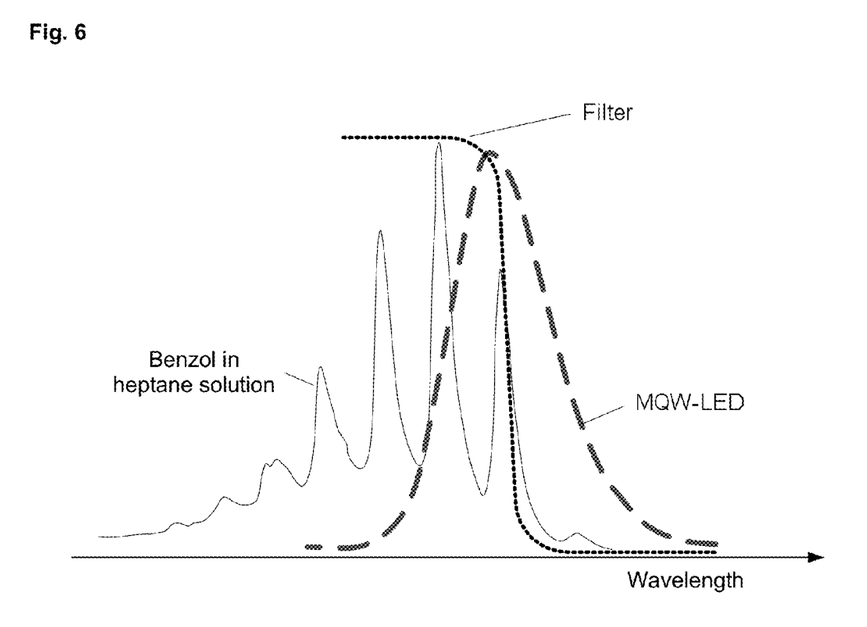

If a bandpass filter is used, then, as shown in FIG. 5, spectrally broadband interferences and superimpositions of the absorptions of other substances are compensated. However, the use of an edge filter, as shown in FIG. 6, represents a somewhat more economical solution.

Figure 7:
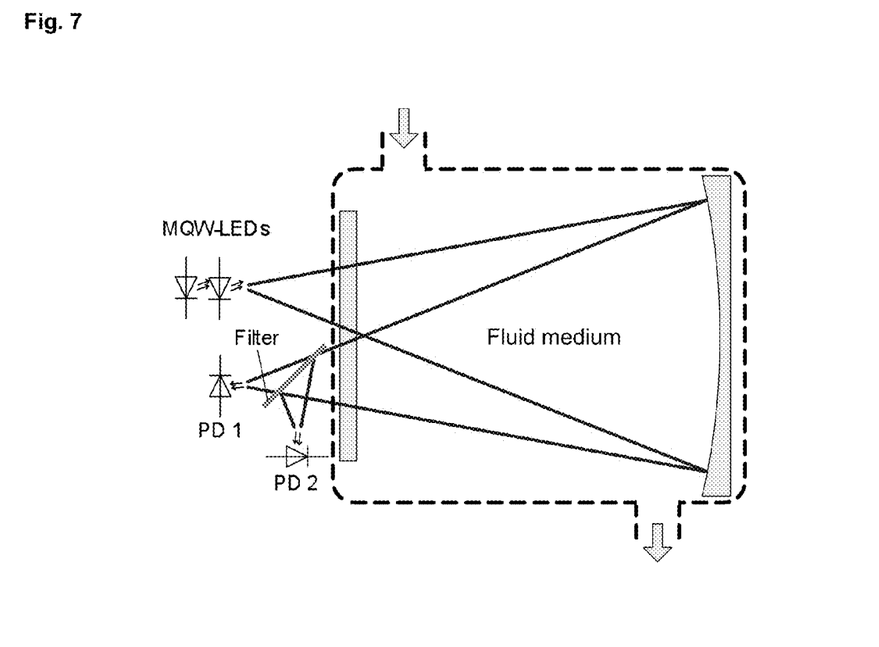
FIG. 7 depicts an example arrangement that uses spatial optical separation as well as multiplexing techniques, a plurality of MQW LEDs and detector units in one set-up, in order to determine the concentration of a plurality of substances in one set-up and compensate any cross sensitivity.
Figure 8:
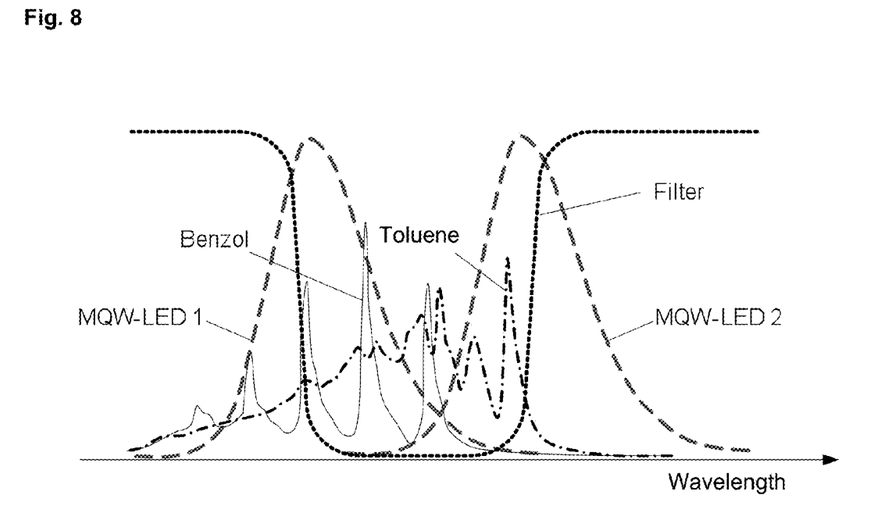
FIG. 8 is a graphic representation of a detector unit of FIG. 7, namely two MQW LEDs acting in the multiplex technique on just one detector unit with a bandpass filter (cf.

Using spatial optical separation as well as multiplexing techniques, a plurality of MQW LEDs and detector units can be used in one set-up, in order to determine the concentration of a plurality of substances in one set-up and compensate any cross sensitivity. An example of such an arrangement is shown in FIG. 7. In this case, two MQW LEDs act in the multiplex technique on just one detector unit with a bandpass filter (cf. FIG. 8). In this way, the selective detection even of a plurality of substances can be achieved very simply and economically.

The device according to the invention makes it possible to amplify and optionally digitise the receiving signals of the absorption detector and reference detector either still within the device or in a connected device. For example, the signals are amplified logarithmically and subtracted from one another in analogue fashion, to produce an analogue signal proportional to the concentration of the substance to be determined, which can be displayed or digitised and processed correspondingly.

To improve the spectral emission stability and to increase the optical output and LED service life, the MQW LED used in the device according to the invention can be actively cooled.

If the device according to the invention is to be used for simultaneously determining the concentrations of a plurality of substances in the fluid, a plurality of MQW LEDs can be used, which are for example electrically modulated. Another advantage of electrical modulation of the MQW LED is improvement of the signal-to-noise ratio of the measurement and suppression of interference.

Figure 9:
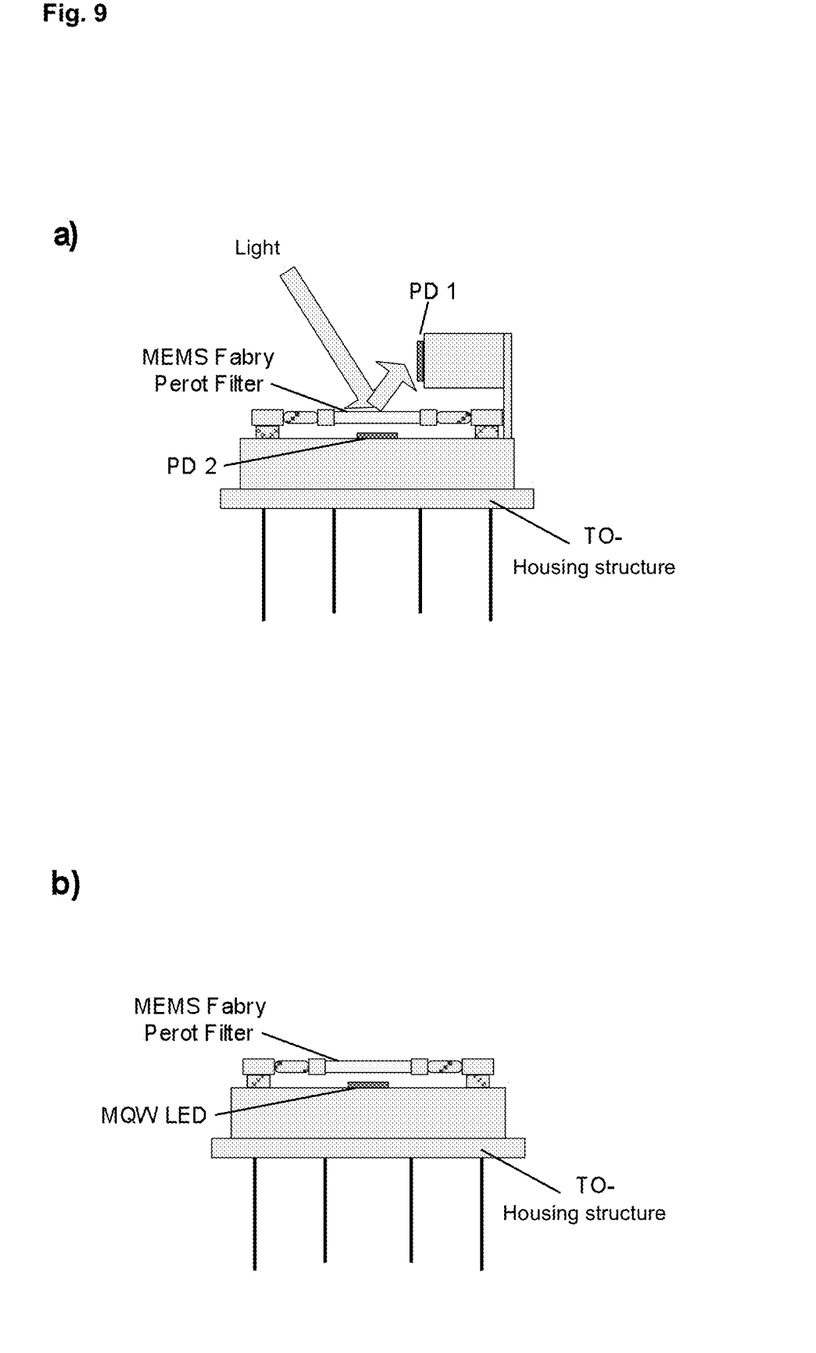
FIG. 9 is a schematic representation of another embodiment of a device according to the present invention that includes a variable filter. The variable filter can be integrated into the detector unit (FIG. 9a) or, alternatively or additionally, can be installed before the MQW LED (FIG. 9b).

In another embodiment, the device according to the invention makes it possible to use a variable optical filter, and the variable filter is preferably a Fabry-Perot filter in MEMS technology. The variable filter can, as shown schematically in FIG. 9, be integrated into the detector unit (FIG. 9a). Alternatively or additionally, the variable filter can be installed before the MQW LED (FIG. 9b), and the MQW LED can for example be integrated in the structure of the variable filter.

All publications, patent applications, patents and other references mentioned herein are incorporated by reference in their entirety.

While the invention has been described in detail and with reference to specific embodiments thereof, it will be apparent to one skilled in the art that various changes and modifications can be made therein without departing from the spirit and scope of the invention.

The invention claimed is:

1. A device for determining the concentration of one or more substances with primarily narrow band absorption characteristics in a fluid medium, wherein said device comprises: (1) an MQW LED having a spectrally limited emission bandwidth and high spectral stability that emits light suitable for absorption measurement, (2) a measuring system in which the light emitted by said MQW LED interacts with the one or more substances with primarily narrow band absorption characteristics whose concentration is to be determined, and (3) a detector unit comprising an optical filter, an absorption detector and a reference detector, wherein said optical filter comprises (a) at least one edge filter or (b) at least one bandpass filter with one or a plurality of bandpass characteristics, further wherein said optical filter divides the spectrum of the light emitted by said MQW LED into at least two spectral parts after having passed said fluid medium, which then act upon said absorption detector and reference detector to generate a measurement signal and a reference signal, respectively, whereby the concentration of the one or more substances to be determined is found by comparing these generated signals.

2. The device according to claim 1, characterised in that said optical filter comprises at least one edge filter.

3. The device according to claim 2, wherein the at least one edge filter is designed as short-wavelength or long-wavelength pass filter.

4. The device according to claim 1, characterised in that said optical filter comprises at least one bandpass filter with one or a plurality of bandpass characteristics.

5. The device according to claim 4, characterised in that the at least one bandpass filter is designed so that the concentration of a plurality of substances can be determined by using a plurality of MQW LEDs.

6. The device according to claim 1, characterised in that the MQW LED is actively cooled.

7. The device according to claim 1, characterised in that the MQW LED is electrically modulated.

8. The device according to claim 1, characterised in that a plurality of MQW LEDs act upon at least one detector unit.

9. The device according to claim 1, characterised in that the optical filter is variable.

10. The device according to claim 9, characterised in that the variable filter is constructed as a Fabry-Perot filter in MEMS technology.

11. The device according to claim 9, characterised in that the variable filter is applied exclusively or additionally before the MQW LED.

12. The device according to claim 11, characterised in that the MQW LED is integrated in the structure of the variable filter.

13. A method for determining the concentration of one or more substances with primarily narrow band absorption characteristics in a fluid medium, said method comprising the steps of:
(a) providing a device for determining the concentration of one or more substances in a fluid medium, wherein said device comprises: (1) an MQW LED having a spectrally limited emission bandwidth and high spectral stability that emits light suitable for absorption measurement, (2) a measuring system in which the light emitted by said MQW LED interacts with the one or more substances with primarily narrow band absorption characteristics whose concentration is to be determined, and (3) a detector unit comprising an optical filter, an absorption detector and a reference detector, wherein said optical filter comprises (a) at least one edge filter or (b) at least one bandpass filter with one or a plurality of bandpass characteristics, further wherein said optical filter divides the spectrum of the light emitted by said MQW LED into at least two spectral parts after having passed the fluid medium, which then act upon said absorption detector and reference detector to generate a measurement signal and a reference signal, respectively;
(b) introducing the one or more substances into said detector unit and generating said measurement signal and reference signal, respectively; and
(c) determining the concentration of the one or more substances by comparing the measurement signal with the reference signal.

14. The method according to claim 13, characterised in that substance(s) with broadband absorption characteristics are detected by means of the edge of an absorption band.

15. The method according to claim 13, characterised in that measurement takes place continuously.

* * * * *